US009233124B2

(12) United States Patent
Balaguer et al.

(10) Patent No.: US 9,233,124 B2
(45) Date of Patent: *Jan. 12, 2016

(54) BIOMATERIALS CONTAINING CALCIUM PHOSPHATE

(75) Inventors: Thierry Balaguer, Colomars (FR); Nathalie Rochet, Nice (FR); Georges Carle, Nice (FR)

(73) Assignees: Centre National de la Recherche Scientifique, Paris (FR); Centre Hospitalier Universitaire De Nice, Nice (FR)

( * ) Notice: Subject to any disclaimer, the term of this patent is extended or adjusted under 35 U.S.C. 154(b) by 598 days.

This patent is subject to a terminal disclaimer.

(21) Appl. No.: 13/000,653

(22) PCT Filed: Jun. 22, 2009

(86) PCT No.: PCT/FR2009/000748
§ 371 (c)(1),
(2), (4) Date: Mar. 24, 2011

(87) PCT Pub. No.: WO2010/007229
PCT Pub. Date: Jan. 21, 2010

(65) Prior Publication Data
US 2011/0178525 A1 Jul. 21, 2011

(30) Foreign Application Priority Data

Jun. 23, 2008 (FR) ..................................... 08 03493

(51) Int. Cl.
*A61F 2/28* (2006.01)
*A61M 39/08* (2006.01)
*A61K 33/42* (2006.01)
*A61L 27/12* (2006.01)
*A61L 27/54* (2006.01)
*A61B 17/88* (2006.01)
*A61K 33/14* (2006.01)

(52) U.S. Cl.
CPC ............ *A61K 33/42* (2013.01); *A61B 17/8805* (2013.01); *A61K 33/14* (2013.01); *A61L 27/12* (2013.01); *A61L 27/54* (2013.01); *A61L 2300/102* (2013.01); *A61L 2300/418* (2013.01); *A61L 2430/02* (2013.01)

(58) Field of Classification Search
USPC .................... 523/114, 115; 424/423; 606/92; 604/93.01
See application file for complete search history.

(56) References Cited

U.S. PATENT DOCUMENTS

| 7,326,464 | B2 | 2/2008 | Lemaitre et al. | |
| 7,357,941 | B2 | 4/2008 | Dalal et al. | |
| 2002/0127720 | A1* | 9/2002 | Erbe et al. | 435/395 |
| 2002/0161449 | A1 | 10/2002 | Muschler | |
| 2003/0198687 | A1* | 10/2003 | Bennett et al. | 424/532 |
| 2004/0101960 | A1 | 5/2004 | Schaefer et al. | |
| 2005/0226939 | A1 | 10/2005 | Ramalingam et al. | |
| 2006/0184131 | A1* | 8/2006 | Murphy et al. | 604/187 |
| 2007/0004035 | A1* | 1/2007 | Sitzmann | 435/325 |
| 2008/0147065 | A1 | 6/2008 | McKay et al. | |
| 2008/0281431 | A1 | 11/2008 | Missos | |
| 2008/0316855 | A1 | 12/2008 | Ferrante et al. | |
| 2009/0275540 | A1* | 11/2009 | Bertelsen et al. | 514/167 |
| 2010/0324500 | A1 | 12/2010 | Buckland et al. | |
| 2011/0182950 | A1 | 7/2011 | Balaguer et al. | |

FOREIGN PATENT DOCUMENTS

| CN | 1923300 | | 3/2007 |
| CN | 1972882 | A | 5/2007 |
| EP | 0 166 263 | A1 | 1/1986 |
| JP | S-60/256460 | A | 12/1985 |
| JP | S-60/256461 | A | 12/1985 |
| JP | H-01/131667 | A | 5/1989 |
| JP | H-01/288269 | A | 11/1989 |
| JP | H-04/322656 | A | 11/1992 |
| JP | 2003/514625 | A | 4/2003 |
| JP | 2004/329458 | A | 11/2004 |
| JP | 2004/97259 | A | 2/2005 |
| JP | 2006/230817 | A | 9/2006 |
| JP | 2009/551262 | | 6/2010 |
| RU | 2224549 | | 2/2004 |
| WO | WO 01/81243 | A1 | 11/2001 |
| WO | WO-02/40071 | A1 | 5/2002 |
| WO | WO 02/068010 | A1 | 9/2002 |
| WO | 2006 015275 | | 2/2006 |
| WO | 2006 058153 | | 6/2006 |
| WO | 2008 104762 | | 9/2008 |

OTHER PUBLICATIONS

Bouler, J.M. et al., *In Vitro Carbonated Apatite Precipitation on Biphasic Calcium Phosphate Pellets Presenting Various HA/β-TCP Ratios*, Key Engineering Materials 2001; 192-195: 119-122.
Bouler et al., *Macroporous Biphasic Calcium Phosphate Ceramics: Influence of Five Synthesis Parameters on Compressive Strength*, J Biomed Mater Res, 1996, 32, 603-609.
Bouler et al., *Biphasic Calcium Phosphates: influence of Three Synthesis Parameters on the HA/β-TCP Radio*, J Biomed Mater Res, 2000, 51 680-684.
Cavagna, R. et al., *Macroporous Calcium Phosphate Cermaic: A Prospective Study of 106 Cases in Lumbar Spinal Fusion*, J. Long-Term effect of Med. Impl 1999; 9:403-412.
Daculsi, G et al., *Transformation of Biphasic Calcium Phosphate Ceramics In Vivo: Ultrastructural and Physiochemical Characterization*, J. Biomed Mater Res 1989; 23: 883-94.
Daculsi et al., Int. Rev. Cytol 1997; 129-191.

(Continued)

Primary Examiner — Tae H Yoon
(74) Attorney, Agent, or Firm — Alston & Bird LLP

(57) ABSTRACT

The invention relates to a biomaterial containing calcium phosphate, in particular hydroxyapatite or a material containing hydroxyapatite, such as biphasic calcium phosphates and calcium phosphate cements, and to the use thereof for the production of an implant or for fitting a prosthesis for the purpose of bone tissue regeneration.

8 Claims, 5 Drawing Sheets

(56) References Cited

OTHER PUBLICATIONS

Effinger, R. f. et al., *Histological Assessment of Periodontal Osseous Defects Following Implantation of Hydroxyapatite and Biphasic Calcium Phosphate Ceramics; A Case Report*, J. Periodontics Restorative Dent 1986; 6:22-33.

Gouin F. et al., *Comblements Osseux Par Céramique Phosphocalcique Biphasée Macroporeuse*, Rev Chir Orthop Reparatrice Appar Mot 1995; 81: 59-65.

Hing, K. A. et al., *Microporosity Enhances Bioactivity of synthetic Bone Graft Substitutes*, Journal of Materials Science: Materials in Medicine, vol. 16, No. 5, (2005) 467-475.

Lerouxel et al., *Injectable Calcium Phosphate Scaffold and Bone Marrow Graft for Bone Reconstruction in Irradiated Areas: An Experimental Study in Rats*, Biomaterials, Sep. 27, 2006(26): 4566-72, 18, 287-294.

Malard, O. et al., *Influence of Biphasic Calcium Phosphate Granulometry on Bone Ingrowth, Ceramic Resorption, and Inflammatory Reactions: Preliminary In Vitro and In Vivo Study*, J. Biomed. Mater. Res. 46(1), 1999, 103.

Nery et al., *Tissue Response to Biphasic Calcium Phosphate Ceramic With Different Ratios of HA/βTCP in Periodontal Osseous Defects*, J. Periodontol. Sep. 1992;63(9): 729-35.

Obadia et al., *Calcium-Deficient Apatite Synthesized by Ammonia Hydrolysis of Dicalcium Phosphate Dihydrate: Influence of Temperature, Time, and Pressure*, J Biomed Mater Res, 2006, 80(B), 32-42.

Okazaki, L. et al., *Blood-Filled Spaces With and Without Deproteinized Bone Grafts in Guided Bone Regeneration*, Clin. Oral Impl. Res., 16, 2005, 236-243.

Passuti, N. et al., *Macroporous Calcium Phosphate Ceramic Performance in Human Spine Fusion*, Clin Orthop Relat Res 1989; (248): 169-76.

Ransford, A. O. et al., *Synthetic Porous Ceramic Compared With Autograft in Scoliosis Surgery*, J Bone Joint Surg Br 1998; 80: 13-8.

Trojani, C. et al., *Ectopic Bone Formation Using an Injectable Biphasic Calcium Phosphate/Si-HPMC Hydrogel Composite Loaded With Undifferentiated Bone Marrow Stromal Cells*, Biomaterials, 27, 2006, 3256-3264.

Yamada, S. et al., *Osteoclastic Resorption of Calcium Phosphate Ceramics With Different Hydroxyapatite/β-Tricalcium Phosphate Ratios*, Biomaterials 1997; 18: 1037-41.

Yamada, S. et al., *Osteoclastic Resporption fo Biphasic Calcium Phosphate Ceramic In Vitro*, J. Biomed. Mater. Res 1997; 37: 346-52.

International Search Report for Application No. PCT/FR09/000749 dated Oct. 15, 2009.

Mankani, M.H., et al., "In Vivo Bone Formation by Human Bone Marrow Stromal Cells: Effect of Carrier Particle Size and Shape," Biotechnology and Bioengineering, vol. 72, No. 1, pp. 96-107, (Jan. 5, 2001) XP 002514537.

Hertz, A., et al., "Inorganic materials for bone repair or replacement applications," Nanomedicine, vol. 2, No. 6, pp. 899-918, (2007) XP 008102023.

International Search Report issued Oct. 16, 2009 in PCT/FR09/000748 filed Jun. 22, 2009.

Chinese Office Action for Application No. 200980131750.X dated Feb. 20, 2013.

Russian Office Action for Application No. 2011102372/15 dated Feb. 7, 2013.

Office Action from U.S. Appl. No. 13/923,577, dated Sep. 29, 2014.

Written Opinion from International Application No. PCT/FR2009/000748 dated Jun. 22, 2009.

Written Opinion from International Application No. PCT/FR2009/000749 dated Oct. 15, 2009.

\* cited by examiner

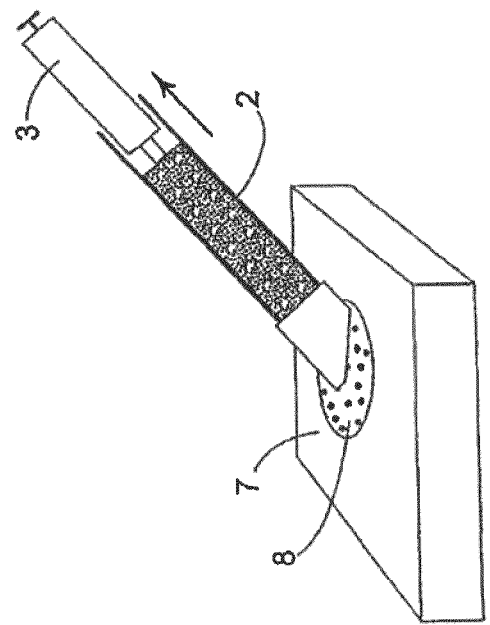
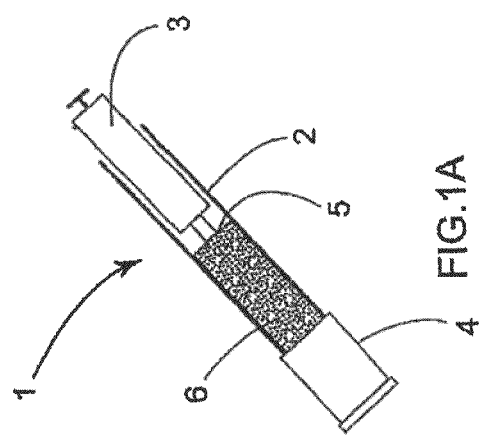
FIG.1A
FIG.1B

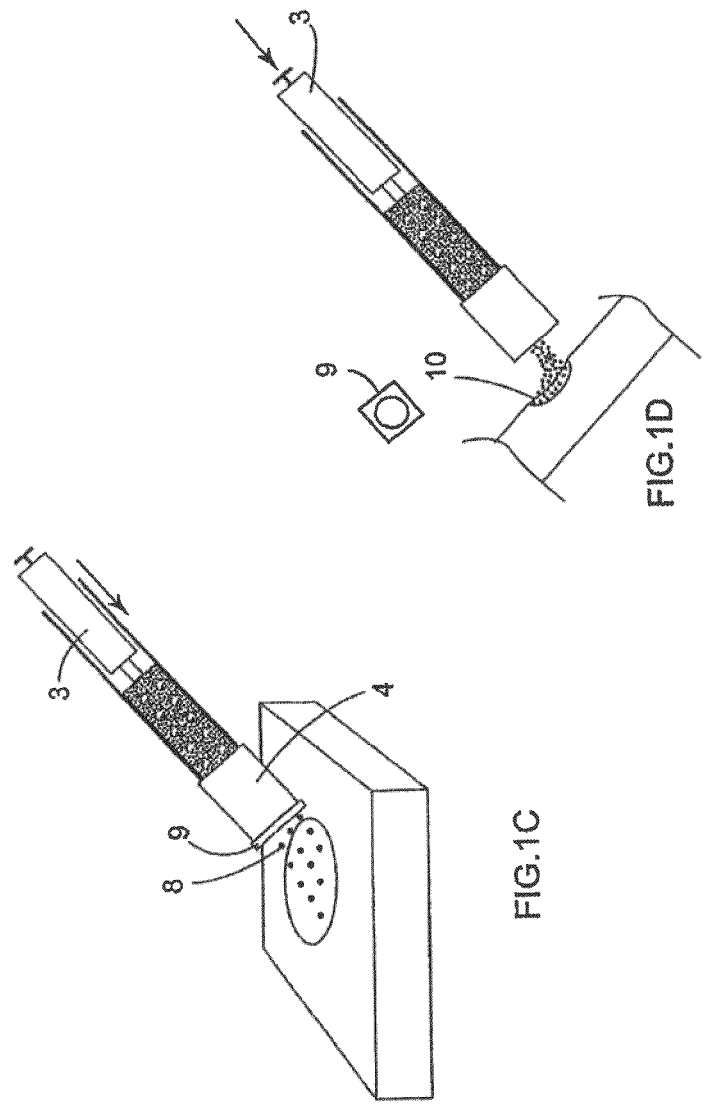

BIOMATERIALS CONTAINING CALCIUM PHOSPHATE

CROSS REFERENCE TO RELATED APPLICATIONS

This application is a national phase entry of International Application No. PCT/FR2009/000748 filed Jun. 22, 2009, which claims priority to French Application No. 08 03493 filed Jun. 2, 2008, the entire contents of which are incorporated herein by reference.

The subject of the invention is a novel biomaterial based on calcium phosphate, in particular based on hydroxyapatite or based on a material comprising hydroxyapatite, such as biphasic calcium phosphates and calcium phosphate cements, a method for the preparation thereof and the use thereof for the production of an implant or for fitting a prosthesis for the purpose of bone tissue regeneration.

The reconstruction of bone substance losses, mainly resulting from trauma and, more rarely, tumor, is one of the major difficulties encountered by orthopedic surgeons. Small defects, from "tight" pseudarthrosis (faulty consolidation of a fracture where the loss of substance is virtual) up to bone losses of 5-6 cm, are most commonly the subject of an autologous graft of spongy or cortical-spongy bone tissues taken from the iliac crest (gold standard). Large defects 6 cm) require much more cumbersome procedures, vascularized bone transfers or a Masquelet procedure. Even so, the amount of autologous bone that is available is limited, the bone consolidation remains random and these various techniques are very much purveyors of post-operative complications at the site where the graft is taken.

Various biomaterials available in clinical practice make it possible to avoid, in theory, the drawbacks of autologous grafting. Unfortunately, none of them equals the results of bone grafting and they never enable the reconstruction of large losses of substances.

The majority of the materials currently studied combine, with the biomaterials, mesenchymal stem cells obtained from bone marrow after several weeks of selection and cell culture in vitro. This approach is laborious and expensive, which limits the clinical uses.

It is known that coagulated blood promotes bone reconstruction. L. Okazaki et al., Clin. Oral Impl. Res., 16, 2005, 236-243 describes implants based on coagulated blood or demineralized bone powder. Document WO 02/068010 describes a bone marrow-based composite material, this material comprising a porous, biocompatible implantable matrix and a coagulated material, such as a bone marrow, blood or plasma coagulate.

Such materials, resulting from the combination of a support and of coagulated or noncoagulated blood, have up until now been used in maxillofacial surgery where the problems of bone consolidation are not so important, but have been used little or not at all in the repair of diaphyseal bones.

The methods for producing these implants require blood to be taken from a donor, most commonly the individual for whom the implant is intended, and then require steps in which the support (demineralized bone or synthetic polymer, ceramic) is handled, in particular steps of mixing with the blood, which are sources of contamination of the biomaterial. In addition, it is difficult to obtain a homogeneous biomaterial by means of these methods.

There thus remains the need for a method for preparing an implantable biomaterial from a support which is synthetic, and therefore easy to produce, with constant and homogeneous properties, this method making it possible to obtain properties that are superior in terms of biocompatibility and enabling the rapid reconstruction of a bone tissue of quality, without it being necessary to use culturing or sampling steps.

The invention makes it possible to remedy the drawbacks of the prior art and enables a bone of excellent quality in terms of hardness and vascularization to be obtained. In addition, the method for producing this biomaterial is simple and easy to carry out, does not require multiple procedures on the individual to be treated, and is relatively inexpensive compared with the prior art methods.

Hydroxyapatite is part of the composition of many bone reconstruction materials. Hydroxyapatite can be used alone in this application or as a mixture with other components, as is the case, for example, in biphasic calcium phosphate or in calcium phosphate cements.

Biphasic calcium phosphate, BCP, is used in many medical and dental applications. Biphasic calcium phosphate was described for the first time as a bone repair material by Nery et al., J Periodontol. 1992, September; 63(9): 729-35. BCP consists of a mixture of hydroxyapatite (HA) $Ca_{10}(PO_4)_6(OH)_2$ and of beta tricalcium phosphate $(Ca_3(PO_4)_2)(\beta\text{-TCP})$. Its bioactivity and its bioresorbability can be controlled through the proportion of hydroxyapatite and of $\beta$-TCP of which it is formed.

Document US-2005/0226939 describes a method for producing hydroxyapatite nanoparticles, this method comprising the mixing of a composition based on calcium ions and on phosphate ions and a microwave treatment. The conditions used in this document do not result in the formation of hydroxyapatite or of BCP impregnated with a calcium chloride solution.

BCP-based biomaterials have the advantage, compared with the other synthetic biomaterials, of promoting osteogenesis.

BCP has been the subject of many studies: Lerouxel et al., Biomaterials, 2006, September 27(26): 4566-72, 18, 287-294; Malard O. et al., J. Biomed. Mater. Res., 46(1), 1999, 103; Mankani M. H. et al., Biotechnology and Bioengineering, 72(1), 2001, 96-107. These various authors have made observations relating to the influence of the size of the BCP particles. In the document Mankani M. H. et al., the method comprises mixing HA/TCP particles with cells then fibrinogen, and thrombin reconstituted in a $CaCl_2$ solution. However, the $CaCl_2$ solution is more concentrated than that used in the invention and the $CaCl_2$/BCP mole/weight ratio is higher than that used in the biomaterials of the invention.

Trojani C. et al., Biomaterials, 27, 2006, 3256-3264, have shown that good osteoinduction can be obtained for the implantation of a BCP/Si-hydroxypropylmethylcellulose hydrogel composite material to which bone marrow cells have been added, with calibrated BCP particles of 40 to 80 μm. The latter methods require, however, a step in which a sample of bone marrow cells is taken and also the culturing of said bone marrow cells.

Document WO 2006/015275 describes a method for enhancing bone regeneration, this method comprising the preparation of a composition consisting of a support material based on calcium phosphate, a platelet-rich plasma, calcium and a PAR receptor activator other than thrombin. However, the $CaCl_2$ concentration in these compositions is so high that, if it were used under the conditions in the present invention, it would act as an anticoagulant.

The two BCP components, HA and $\beta$-TCP, represent the two main types of calcium phosphates used in bone and dental surgery. They are remarkably biocompatible and it is considered that combining them provides a better bioactivity and therefore greater efficacy than HA alone or β-TCP alone. This is because, in BCPs, the two components (HA and β-TCP) exhibit a synergistic action:

Hydroxyapatite, as soon as it is implanted in vivo and by virtue of its chemical nature, can promote, at its surface, the formation of multisubstituted non-stoichiometric calcium phosphate apatite (known as "biological apatites") by epitaxial growth. This layer of biological apatite, which is very similar to the crystals present in the bone matrix, is thought to facilitate cell adhesion and cell activity.

β-TCP, which is much more soluble than HA, maintains a supersaturation of calcium and phosphates in the biological fluids surrounding the BCP implant. This makes it possible to maintain the phenomenon of precipitation of biological apatite on the HA phase. In addition, this phase is much more resorbable than HA, and it is therefore possible to modulate the resorbability of the implant by varying the HA/β-TCP ratio.

These chemical phenomena have been shown in vitro (J. M. Bouler, G. Daculsi, Key Engineering Materials 2001; 192-195: 119-122; Yamada S, et al., Biomaterials 1997; 18: 1037-41; S. Yamada et al., J. Biomed. Mater. Res 1997; 37: 346-52) and in vivo (Daculsi G. et al., J. Biomed Mater Res 1989; 23: 883-94; G. Daculsi et al., Int. Rev. Cytol 1997; 129-191). These mechanisms seem to contribute to the better clinical efficacy of BCPs compared with single-phase HA or TCP materials (Nery E B et al., J Periodontol 1992; 63: 729-35; Ellinger R F et al., J Periodontics Restorative Dent 1986; 6:22-33; Passuti N. et al., Clin Orthop Relat Res 1989; (248): 169-76; Gouin F et al., Rev Chir Orthop Reparatrice Appar Mot 1995; 81: 59-65; Ransford A O et al., J Bone Joint Surg Br 1998; 80: 13-8; R. Cavagna et al., J. Long-Term effect of Med. Impl 1999; 9:403-412).

The present invention is based on the observation that certain calcium phosphates, in particular calcium phosphate apatites, such as hydroxyapatite, inhibit the spontaneous coagulation of whole blood when they are brought into contact. Specifically, it has been observed that HA, and also BCP, which contains HA, inhibit the spontaneous coagulation of whole blood when they are brought into contact. It has also been observed that, if the hydroxyapatite or the BCP is pre-impregnated with physiological saline (which is an aqueous phase of NaCl), as recommended in the instructions of using these biomaterials, the blood subsequently brought into contact does not coagulate.

Experimental conditions which make it possible to establish the anticoagulant properties of a support material are detailed in the experimental section.

The first subject of the invention is a method for preparing an implantable biomaterial comprising a support based on at least one calcium phosphate, such as hydroxyapatite or a mixture of hydroxyapatite and of at least one other material, this method comprising at least one step of impregnation of the support with at least one coagulating agent.

The expression "support based on calcium phosphate" is intended to mean a material comprising at least one constituent of calcium phosphate apatite type chosen from: hydroxyapatite, fluoroapatite, multisubstituted non-stoichiometric apatites (ms-ns-AP) and also mixtures thereof along with other calcium phosphate biomaterials. Such supports may be constituted of hydroxyapatite, BCP, ms-ns-APs and apatite calcium phosphate cements.

The support thus impregnated is then implanted on the site where a bone defect must be filled. The implantation of said support then causes coagulation of the blood which comes into contact with the biomaterial which penetrates into the biomaterial in situ. In the trials that have been carried out with BCP, it has been observed that BCP, combined with coagulated blood, makes it possible to obtain good osteogenesis and results in a bone tissue of very satisfactory quality by means of a method which is very simple compared with those of the prior art. Without impregnation of the BCP with a solution of coagulating agent, no osteogenesis is obtained.

According to one variant of the invention, the support based on calcium phosphate, in particular based on hydroxyapatite or on a mixture of hydroxyapatite and another material, is implanted in the site where a bone defect must be filled, and is then impregnated in situ with a solution of coagulating agent.

Preferably, the support used in the invention is based on hydroxyapatite, fluoroapatite, multisubstituted non-stoichiometric apatites (ms-ns-AP) or a mixture of one of these compounds with at least one other biomaterial, such as tricalcium phosphate in α and β form ($Ca_3(PO_4)_2$), dicalcium phosphate dihydrate ($CaHPO_4.2H_2O$), anhydrous dicalcium phosphate ($Ca(HPO_4)$), monocalcium phosphate monohydrate ($Ca(HPO_4)_2.H_2O$), tetracalcium phosphate ($Ca(PO_4)_2O$) and octacalcium phosphate ($Ca_8H_2(PO_4)_6$). Advantageously, the support is based on hydroxyapatite or on BCP, it is preferably based on BCP.

The support, and in particular the apatite or the BCP, which can be used in the invention can be in any form: either in the form of a monolith or in the form of granules, calibrated or not.

The BCP which can be used in the invention consists of a high temperature frit. When it is granule form, it is ground and calibrated, for example by screening, according to the chosen diameter. Advantageously, the BCP which can be used in the invention comprises hydroxyapatite and β-tricalcium phosphate in an HA/β-TCP weight/weight ratio of between 5/95 and 95/5, preferably between 30/70 and 80/20, advantageously between 40/60 and 60/40.

Advantageously, this involves a porous support, and in particular a porous BCP, with pore sizes ranging from 50 nm to 1000 μm, advantageously from 500 nm to 100 μm, and more advantageously from 1 μm to 50 μm.

When the support, and in particular the BCP, used in the present invention is in granule form, it advantageously has a particle size of between 40 and 500 μm, preferably between 40 and 400 μm, even more preferably between 40 and 300 μm, and advantageously between 80 and 200 μm.

The BCP granules or powder can be obtained in accordance with the methods described by Bouler et al., J Biomed Mater Res, 1996, 32, 603-609; Bouler et al., J Biomed Mater Res, 2000, 51, 680-684; Obadia et al., J Biomed Mater Res, 2006, 80(B), 32-42.

The BCP can be obtained commercially from the company Graftys SARL (Aix en Provence).

The hydroxyapatite that can be used in the invention is preferably in granule form. It is commercially from the company Graftys SARL.

More particularly, the invention relates to a biomaterial comprising a calcium phosphate-based support, impregnated with a solution of at least one calcium-derived coagulating agent, the support being chosen from: hydroxyapatite and a BCP, the coagulating agent being in the form of an aqueous solution having a concentration ranging from 1 to 50 mMol/l, the proportion of coagulating agent solution and of HA or of BCP being from 0.5 to 5 by volume/volume of coagulating agent solution relative to the volume of HA or of BCP.

Preferably, the invention relates to a biomaterial comprising a calcium phosphate-based support, impregnated with a solution of at least one calcium-derived coagulating agent, the support being chosen from: hydroxyapatite and a BCP, the calcium-derived coagulating agent being present in a proportion ranging from 2.5 to 60 µmol of calcium per gram of HA or of BCP, and preferably from 5 to 40 µmol of calcium per gram of HA or of BCP.

The coagulating agent is a calcium-based coagulating agent, such as a biocompatible calcium salt, for instance: $CaCl_2$, $Ca(NO_3)_2$, $Ca(EtOAc)_2$ or $CaSO_4$.

Advantageously, the coagulating agent is calcium-based and it is chosen from biocompatible calcium salts, advantageously $CaCl_2$. In order to allow the impregnation of the support, in particular the HA or the BCP, with the coagulating agent, the latter is used in an aqueous solution, advantageously in an aqueous solution having a concentration ranging from 1 to 50 mMol/l, preferably from 3 to 40 mMol/l, advantageously from 5 to 20 mMol/l. These values are particularly preferred when the coagulating agent is a calcium salt, and in particular $CaCl_2$.

The proportion of coagulating agent solution and of HA or of BCP used in the method of the invention is from 0.5 to 5 by volume/volume of coagulating agent solution relative to the weight of HA or of BCP, preferably from 1 to 3, advantageously approximately 2.

According to another variant of the invention, the biomaterial is prepared extemporaneously by impregnation of the calcium phosphate-based support just before implantation thereof.

It is also possible to envision preparing the biomaterial of the invention by applying the following procedure: impregnating the calcium phosphate-based support with a coagulating agent solution, then drying it or freeze-drying it, and then packaging it under sterile conditions and storing it until its implantation.

Advantageously, the impregnation time is from 1 minute to 1 hour, preferably from 1 to 30 minutes, advantageously from 5 to 15 minutes.

According to another variant of the invention, a biomaterial of the invention can be prepared by impregnating the calcium phosphate-based support with a coagulating agent solution, and then this biomaterial is packaged under sterile conditions and is thus stored until its implantation.

According to one variant of the invention, it is possible to envision that the (calcium phosphate-based) support biomaterial is combined with the coagulating agent in powder form. In particular, a biomaterial such as BCP or HA in powder or granule form can be mixed with a calcium salt in solid powder form. This biomaterial may thus be stored until its use, and impregnated with an aqueous solution, for instance physiological saline, extemporaneously, just before its implantation, at the time of its use. It can thus be implanted in nonimpregnated, dry form.

According to the invention, it is possible to envision adding to the support, and in particular to the BCP, one or more optional additives such as: polymers, ceramic particles, pharmaceutical molecules, bioactive agents, the conditions for using these materials being: their biocompatibility, an absence of negative effect on the blood coagulation reaction. Should one of these additives have an unfavorable effect on blood coagulation, this should be taken into account in the amount of coagulating agent to be used. For example, such additives or active agents can be used by grafting of the support, BCP or the like, by mixing or impregnation or by coating. Such additives, which are well known to those skilled in the art, are intended to modify the rheology of the biomaterial or its behavior in vivo (hardness, resorption, osteogenesis) or to act on the occurrence of infections or of inflammatory phenomena (antibiotics, anti-infectives, anti-inflammatories).

It is also possible to envision introducing into the biomaterial of the invention one or more therapeutic molecules, such as molecules intended for preventing or treating a pathological condition chosen, for example, from: a cancer and osteoporosis.

It is also possible to envision introducing into the biomaterial of the invention adipose tissue, or any other tissue or cell preparation, taken from the patient for whom the biomaterial is intended, this adipose tissue or this preparation having been suspended beforehand in blood or plasma or physiological saline.

Natural or synthetic growth factors may also be introduced into the biomaterial of the invention. It is also possible to envision the presence of biomarkers or contrast agents which promote the visualization by medical imaging of the resorption of the biomaterial and its fate in the organism.

According to the method of the invention, the support, and in particular the HA or the BCP, is placed in a cavity of a closed and sterile container. When the support is in granule form, it can, for example, be placed in the internal cavity of a syringe. The appropriate amount of coagulating agent is introduced into this container, for example by drawing up using the syringe if such a device is being used.

In the case where the support, and in particular the HA or the BCP, is in the form of a monolith, the latter is placed in a container of appropriate shape and size.

In all cases, the volume of the container is such that it allows the introduction of the desired amount of coagulating agent solution.

The closed container containing the support, in particular the HA or the BCP, and the coagulating agent can be agitated, so as to allow homogeneous impregnation of the biomaterial. However, passive impregnation of the support by the coagulating agent can also be envisioned.

At the end of this step, the biomaterial is in the form of:
a homogeneous liquid paste, when the support has been used in granule form,
a monolith, the cavities of which are filled with liquid, when the support has been used in the form of a monolith.

According to one variant of the invention, it is possible to envision implanting the support material directly in the space to be filled, optionally as a mixture with the coagulating agent in powder form, and then impregnating it in situ, either with coagulating agent solution, or, when it is already in a mixture with the coagulating agent, with a suitable aqueous solution such as physiological saline. It is also possible to envision implanting it, when it is in the form of a dry mixture with the coagulating agent, without impregnating it, and leaving it to be impregnated with the blood from the surrounding tissues.

Another subject of the invention is a biomaterial comprising a support based on calcium phosphate, such as hydroxyapatite or a BCP, impregnated with a solution of at least one coagulating agent, as described above.

According to the physical form of the support, HA or BCP, and the type of device which were used to prepare the biomaterial of the invention, said material can then be applied using the means most suitable for the position where a bone defect must be filled:

Using a tool such as a spatula, or using a syringe, the end of which comprises an opening suitable for the rheology and the size of the particles of the biomaterial of the invention. It can also be implanted directly in the form of a monolith. In the latter case, said monolith will have been designed or trimmed so that its shape and its dimensions correspond to those of the space to be filled.

A subject of the invention is also a method for filling a bone defect, this method comprising the steps listed above and also comprising a step of inserting the biomaterial into the space where a bone defect has been noted. This method may also comprise tissue-incision and suturing steps.

According to the size and the configuration of the bone defect, the filling with the biomaterial of the invention can be combined with the temporary application of an osteosynthesis which gives the affected tissue the necessary mechanical strength while the bone reconstruction takes place on the site of implantation of the biomaterial of the invention.

As the inventors have noted, the implantation of the biomaterial of the invention has made it possible to promote the formation of bone tissue in short periods of time (a few weeks), this bone tissue being very richly vascularized.

Another subject of the invention consists of a kit for carrying out the method of the invention, this kit comprising the combination of a support based on a calcium phosphate such as a hydroxyapatite or a mixture of hydroxyapatite and at least one other material, for instance a microporous BCP, with a calcium-derived coagulating agent. Advantageously, the coagulating agent is a biocompatible calcium salt, such as $CaCl_2$.

The amount of coagulating agent is calculated so as to compensate for the anticoagulant effect of the calcium phosphate, and in particular of the hydroxyapatite, and to promote blood coagulation in the surrounding tissues.

Such a combination may be in the form of a kit comprising: (a) a sterile device comprising a sterile internal cavity in which the support, for instance the BCP or the HA, is placed, (b) a sterile reservoir comprising the coagulating agent.

The reservoir (b) may be part of the device (a) or may be a separate entity such as a tube or a bottle from which the coagulating agent can be taken in order to transfer it into the internal cavity of the device (a), or a syringe which allows the coagulating agent to be injected into the cavity where the support is placed.

The internal cavity of the device (a) is of a size which makes it possible to introduce therein the amount of coagulating agent necessary for producing the biomaterial of the invention, and also the other constituents of the mixture, such as, for example, active ingredients.

Also advantageously, the device (a) comprises means for applying the biomaterial in the region where a bone defect has been noted.

Such a device may consist of a syringe.

It is also possible to envision using a device such as the one described in WO 02/068010 comprising a tube inside which the support, in particular the BCP, is stored and into which the coagulating agent is injected, and for which a plunger can be fitted in order to release the biomaterial once the latter is formed.

A biomaterial according to the invention can be used for the production of a bone implant, whether it is a question of filling a fracture, a loss of substance of traumatic or tumor origin, or a defect following a surgical procedure, or of aiding the fitting of a prosthesis.

The biomaterial can be introduced by means of a surgical procedure in the region where a bone defect must be filled. After incision, the biomaterial is implanted and the incision is closed.

The biomaterial of the invention can be combined with an osteosynthesis so as to allow temporary consolidation while awaiting the stabilization of the defect region by the bone tissues.

Coating of the prosthesis with the biomaterial of the invention makes it possible to promote the implantation of living bone tissue in or around the prosthesis.

The biomaterial of the invention can also be used in vitro or ex vivo as a support for the production of bone tissue:

Specifically, the culturing of bone cells around this biomaterial makes it possible to produce a bone tissue which is subsequently implantable.

Another subject of the invention is the in vitro or ex vivo use of a biomaterial as described above, for producing a bone implant.

According to the invention, bone cells can be cultured on the biomaterial of the invention in a mould having the shape of the prosthesis that it is desired to produce. The culturing of cells under these conditions makes it possible to obtain a biocompatible prosthesis of suitable shape and dimensions.

BRIEF DESCRIPTION OF THE DRAWINGS

FIGS. 1A to 1D: Preparation of the implants and surgical procedure.

EXPERIMENTAL SECTION

Figure 2:
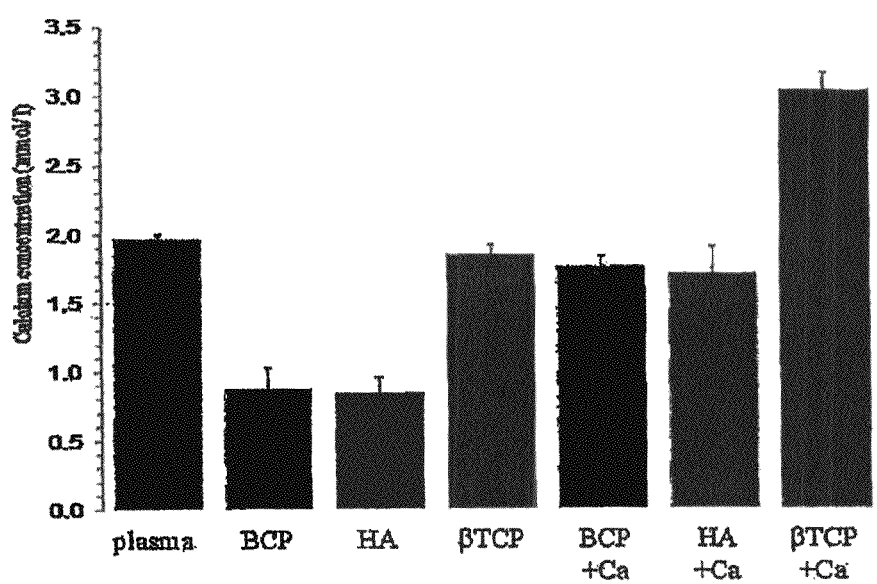
FIG. 2: Graphic illustration of the calcium concentration of a plasma in contact with the calcium phosphate biomaterials.

I—Effect of BCP and of HA on Coagulation

1. Principle:

It involves an extemporaneous procedure carried out in the operating room. It consists in mixing, in the body of a polypropylene syringe, BCP particles and a coagulating agent: $CaCl_2$. The implantation of this biomaterial in the site where a bone defect has been noted promotes coagulation around the biomaterial.

2. Materials and Methods 2.1. Biphasic Calcium Phosphate Particles:

The biphasic calcium phosphate (BCP) biomaterial is composed of 60% of hydroxyapatite (HA; $Ca_{10}(PO_4)_6(OH)_2$) and of 40% of tricalcium phosphate (TCP; $Ca_3(PO_4)_2$). The BCP particles sized between 40 and 200 microns were provided by the company Graftys SARL (Aix-en-Provence, France). The particles were sterilized by heating at 180° C. for two hours.

2.2. Measurement of the Calcium Concentration in Murin Plasma:

The calcium concentration was measured in C57BL/6 mouse (Janvier, Le Genest-St-Isle, France) plasma. This plasma was prepared, from blood taken on heparin, by centrifugation at 1800 g for 15 minutes. Heparin is used as an anticoagulant which does not modify the plasma calcium concentration. The analysis was carried out in a Hitachi automated device (Orléans, France).

2.3. Preparation of Implants and Surgical Procedure:

As illustrated in FIGS. 1A to 1D, a syringe (1) comprising a hollow cylindrical body (2) in which a plunger (3) moves is used. At the end of the body (2) which is not closed off by the plunger, the body of the syringe is closed off by a filter stopper (4). In the body (2) of the syringe, between the end (5) of the plunger and the filter stopper (4), are granules (6) of BCP (FIG. 1A). The whole was sterilized prior to its use. The end of the syringe bearing the filter stopper (4) is placed in a container (7) filled with an aqueous solution (8) of $CaCl_2$ at a concentration of 1%. A backward movement of the plunger (3) allows the solution (8) to be drawn up into the body (2) of the syringe (1) (FIG. 1B). The whole is left to stand for 10 min in order for the BCP particles to impregnate the solution, and then, by means of the plunger (3), the excess solution (8) of the $CaCl_2$ is expelled through the filter stopper (4) (FIG. 1C). The filter (9) is removed from the filter stopper (4) and a pressure on the plunger (3) makes it possible to deposit the BCP granules (6) impregnated with solution (8) on the operating site (10) (FIG. 1D). The implantation site is then closed up again (step not represented).

3. Results 3.1. Effect of Hydroxyapatite and of TCP on Coagulation:

50 mg of HA powder or of TCP powder were placed in the body of a 1 ml syringe. 100 µl of blood were added to each syringe containing either HA or TCP. This mixture was placed on a wheel allowing the powder to remain in suspension in the blood during the coagulation time, i.e. 10 minutes. In each experiment, one syringe containing 100 µl of whole blood treated like the others, i.e. 10 min on the wheel, served as a positive control for the coagulation. After 10 minutes, the wheel is stopped, the syringes are recovered, their end is cut and the blood/powder mixture is extracted by pushing with the syringe plunger. Coagulation of the blood around the powder is or is not observed. Each experiment was repeated 3 times.

It was observed that, in the presence of 50 mg of HA and 100 µl of whole blood, the coagulation was inhibited. The blood remains liquid.

Control: positive control for coagulation. A clot and a serum extrudate were observed.

In the presence of 50 mg of TCP+100 µl of blood, coagulation occurred; this results in the formation of an implant in which the fibrin network keeps the powder homogeneously in suspension.

The same experiment was carried out with calcium chloride having been added to the syringe containing the HA prior to the introduction of blood: coagulation and the formation of an implant were found.

3.2. Effect of BCP on Coagulation

It was observed that blood freshly taken (100 µl) in the absence of anticoagulant and immediately mixed with the BCP particles (50 mg) does not coagulate. This anticoagulant effect is nullified by the addition of $CaCl_2$ (20 µl of a 1% $CaCl_2$ solution) suggesting an uptake of the plasma calcium by the BCP. This hypothesis was confirmed by measuring the calcium concentration in the plasma before and after contact with BCP. For this, plasma was prepared from C57BL/6 mouse blood taken on heparin (anticoagulant which does not modify the plasma calcium concentration). In the presence of BCP, a decrease in the plasma calcium concentration from 2.06±0.06 mmol/l (normal value) to 0.59±0.07 mmol/l in the presence of BCP was observed.

II—Effect of the Calcium Phosphate-Based Biomaterials on Plasma Calcium Concentration 1. Principle:

Aliquots of 50 mg of BCP (60/40) microparticles, or aliquots of 50 mg of HA or of β-TCP were brought into contact with either 50 µl of $H_2O$ or with 50 µl of a 2.5 mM solution of $CaCl_2.2H_2O$, and left to dry overnight at 56° C. These biomaterials were deposited in the wells of a 96-well microplate. 100 µl of plasma prepared from C57BL/6 mouse blood taken on heparin, an anticoagulant which does not interfere with the calcium level, are added to each well. After 15 minutes in incubation, the plate was centrifuged for 2 minutes at 800 g and the supernatants were taken in order to assay the calcium concentration of the plasma. The calcium assay was carried out using the QuantiChrom Calcium Assay kit (Centaur, Brussels, Belgium) and according to the manufacturer's instructions. For this, 5 µl aliquots of supernatant were brought into contact with 200 µl of a solution of phenolsulfonephthalein, a dye which forms a blue-colored stable complex in the presence of free calcium. After incubation for 3 minutes, an intensity of coloration, measured at 612 nm, which is directly proportional to the calcium concentration in the sample, is obtained. In each plate, a calibration range is prepared using the following concentrations of calcium: 0-0.5-1-1.5-2-3-4-5 mM.

2. Results:

It was noted (FIG. 2) that the BCP in microparticle form and also the HA powder, brought into contact with plasma, induced a considerable and significant decrease in the calcium concentration of said plasma. The decrease in calcium concentration is similar for BCP and HA and is not observed for β-TCP. On the basis of the values obtained for the plasma alone (1.960±0.044 mM), the plasma in the presence of BCP (0.871±0.160 mM) and the plasma in the presence of HA (0.840±0.121 mM), the calcium uptake was evaluated at 0.125 µmol of calcium per 50 mg of BCP or HA.

It was also noted that the addition of 50 µl of a 2.5 mM solution (i.e. 0.125 µmol) to the BCP or the HA before addition of the plasma made it possible to restore a normal plasma calcium concentration (FIG. 2). The same amount of calcium chloride added to β-TCP adds to the initial plasma calcium and confirms the absence of uptake by this biomaterial under these conditions.

Moreover, it was observed that the calcium uptake was identical for the three BCP granulosities tested, i.e. for the microparticles of 40-80 µm, of 80-200 µm and those of 200-500 µm.

Furthermore, the same results of compensation through the addition of calcium were obtained whether the calcium chloride solution is added extemporaneously in liquid form just before adding the plasma, or whether this solution is first dried on contact with the particles.

III—Effect of the Addition of Calcium on the Anticoagulant Properties of BCP and of HA 1. Principle:

In order to demonstrate that a cause-and-effect link existed between the inhibition of coagulation and the decrease in plasma calcium induced by BCP and HA, coagulation tests were carried out on aliquots of 50 mg of BCP (60/40) microparticles and of 50 mg of HA powder, after the addition of 50 µl of 150 mM NaCl or of 50 µl of 2.5 mM $CaCl_2.2H_2O$.

Figure 3A:
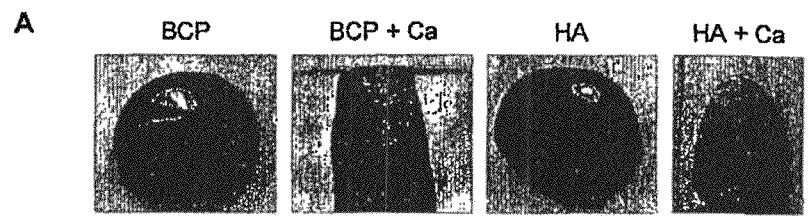
FIG. 3A: Photograph of the product obtained by adding a solution of calcium chloride to BCP and HA before the addition of blood.
Figure 3:
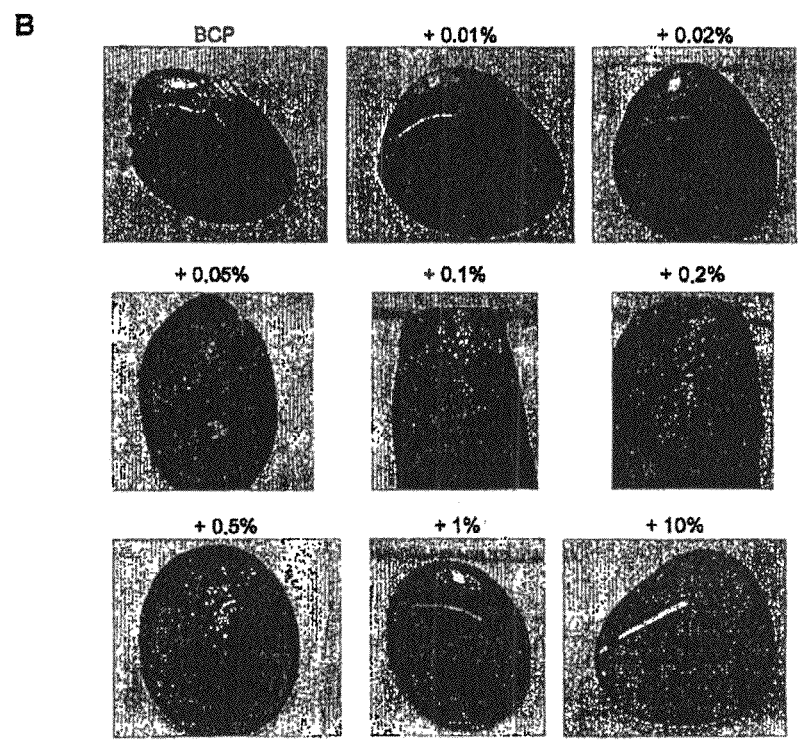
FIG. 3B: Photograph of the product obtained by adding a solution of calcium chloride in increasing concentrations to BCP.

2. Results:

After the addition of the blood not treated with an anticoagulant and rotation for 15 minutes, it was noted (FIG. 3A) that the prior addition of calcium to the BCP and the HA made it possible to reestablish coagulation of the blood brought into contact with these two biomaterials.

These results demonstrate that the anticoagulant effect of the BCP and of the HA is indeed linked to the decrease in the plasma calcium concentration that these two biomaterials induce, and that the addition of calcium makes it possible to reestablish coagulation.

The effect of a calcium dose-response on the coagulation of blood brought into contact with BCP was analyzed (FIG. 3B). The biomaterial was prepared by adding 100 µl of whole blood, not supplemented with an anticoagulant, to 50 mg of BCP particles in the presence of a fixed volume of 50 µl of $CaCl_2 \cdot 2H_2O$, prepared at the concentrations of 0.01% (0.68 mM)-0.02% (1.36 mM)-0.05% (3.4 mM)-0.1% (6.8 mM)-0.2% (13.6 mM)-0.5% (34 mM)-1% (68 mM)-10% (680 mM), or of the same volume of NaCl at 150 mM. After incubation for 15 minutes on a wheel, the biomaterial is demolded. It was noted that, at low concentrations, corresponding here to 0.01% and 0.02%, the added calcium did not make it possible to reestablish coagulation. In the presence of concentrations between 0.05% and 0.5%, coagulation was observed. Surprisingly, it was noted that increasing the concentration of $CaCl_2 \cdot 2H_2O$ to 1% and above induced, once again, inhibition of coagulation (FIG. 3B and table 1).

These experiments made it possible to determine the optimum calcium concentrations which made it possible to block the anticoagulant effect of BCP 60/40 and showed that there is a important concentration range to be respected.

IV. Analysis of the Fibrin Network by Scanning Electron Microscopy

The anticoagulant effect of BCP visualized by the absence of formation of cohesive gelled implants during the tests described above corresponds, at the molecular level, to the inhibition of the formation of the fibrin network forming the framework of the clot. The presence of the fibrin network was analyzed by scanning electron microscopy. For this, implants were prepared by mixing 100 µl of blood, not supplemented with anticoagulant, with 50 mg of BCP or with 50 mg of BCP incubated in the presence of calcium and then dried. After 15 minutes of rotation on a wheel, the mixtures were demolded and directly immersed in a fixing solution containing 1.6% of glutaraldehyde in a 0.1M phosphate buffer, pH 7. The samples were then washed, dehydrated using bowls of alcohol at increasing concentrations, immersed in hexamethyldisilazane (Sigma-Aldrich, Lisle d'Abeau Chesnes, France) for 5 minutes and dried at ambient temperature. After mounting on aluminum supports and covering with gold/palladium for 4 minutes (Polaron, A5100, UK), the analysis is carried out using a scanning electron microscope (JEOL 6700F, Japan).

Figure 4:
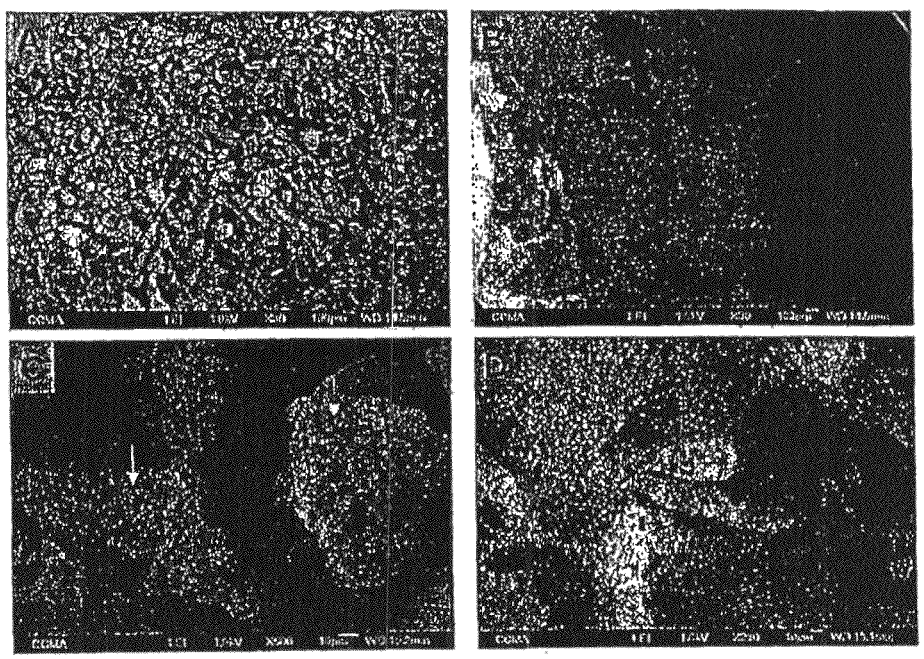
FIG. 4: Scanning electron microscopy analysis of implants consisting of whole blood taken without anticoagulant (A, C) and of BCP microparticles (80-200 μm), or of implants prepared according to the usual protocol (B, D). In the implants prepared without calcium, the absence of formation of a network of fibrin and of a blood clot around the grains is noted (A, C). The white arrow in (C) indicates some red blood cells deposited on the grains. Scales A, B: 100 μm; C, D: 10 μm.

As can be seen in FIG. 4, under the BCP conditions, no fibrin network was observed (FIGS. 4A, 4C) between the BCP microparticles. The presence of a few red blood cells deposited on the grains attest to the mixing of the particles with the blood. Conversely, in the presence of BCP/calcium, the presence of a clot holding the particles is observed, said clot being visualized by the mesh of the fibrin network and a very large number of red blood cells (FIGS. 4B, 4D).

TABLE 1

| Concentration of the $CaCl_2 \cdot 2H_2O$ solution added to the mixture of BCP and blood (as % and as molarity) | Number of µmol of calcium introduced per 50 µl of $CaCl_2 \cdot 2H_2O$ | Coagulation test 50 mg BCP + 100 µl blood + 50 µl $CaCl_2 \cdot 2H_2O$ (liquid or dried) |
|---|---|---|
| 0 | | − |
| 0.01% (0.68 mM) | 0.034 | − |
| 0.02% | 0.068 | + |
| 0.03% | 0.102 | + |
| 0.04% | 0.136 | + |
| 0.05% | 0.17 | + |
| 0.1% | 0.34 | + |
| 0.2% | 0.68 | + |
| 0.5% | 1.7 | + |
| 0.6% | 2.04 | + |
| 0.7% | 2.38 | + |
| 0.8% | 2.72 | + |
| 0.9% | 3.06 | + |
| 1% (68 mM) | 3.4 | +/− |
| 2% | | − |
| 10% (680 mM) | 34 | − |

The invention claimed is:

1. A material for bone tissue regeneration, the material consisting of
   a mixture of an aqueous solution having a calcium comprising coagulating agent and a support material selected from the group consisting of hydroxyapatite (HA) and a biphasic calcium phosphate (BCP), and a combination thereof, wherein the material is a paste and wherein the amount of coagulating agent in the mixture is from 2.5 to 60 µmol of calcium per gram of HA, BCP, or a combination thereof.

2. The material of claim 1, wherein the coagulating agent is $CaCl_2$.

3. The material of claim 1, wherein the support is in granule form.

4. A method for filling a bone defect, the method comprising implanting the material of claim 1 into bone tissue.

5. A combination, consisting of the material of claim 1 and an osteosynthesis.

6. A method of producing bone tissue, comprising combining, in vitro or ex vivo, the material of claim 1 with bone cells.

7. A method of producing bone implant, comprising combining, in vitro or ex vivo, the material of claim 1 with bone cells or a prosthesis mould.

8. The material of claim 1, wherein the coagulating agent is present in a proportion ranging from 5 to 40 µmol of calcium per gram of HA or BCP.

* * * * *